US010610160B1

(12) United States Patent
McNair

(10) Patent No.: US 10,610,160 B1
(45) Date of Patent: Apr. 7, 2020

(54) STREAM-BASED ALARM FILTERING

(71) Applicant: Cerner Innovation, Inc., Kansas City, KS (US)

(72) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 566 days.

(21) Appl. No.: 14/689,343

(22) Filed: Apr. 17, 2015

Related U.S. Application Data

(60) Provisional application No. 61/981,015, filed on Apr. 17, 2014.

(51) Int. Cl.
| | |
|---|---|
| *A61B 5/00* | (2006.01) |
| *A61B 5/0205* | (2006.01) |
| *G08B 21/18* | (2006.01) |
| *A61B 5/145* | (2006.01) |
| *A61B 5/08* | (2006.01) |
| *A61B 5/021* | (2006.01) |
| *A61B 5/024* | (2006.01) |
| *A61B 5/0402* | (2006.01) |

(52) U.S. Cl.
CPC .......... *A61B 5/7225* (2013.01); *A61B 5/0205* (2013.01); *A61B 5/746* (2013.01); *G08B 21/182* (2013.01); *A61B 5/021* (2013.01); *A61B 5/024* (2013.01); *A61B 5/0402* (2013.01); *A61B 5/0816* (2013.01); *A61B 5/14542* (2013.01)

(58) Field of Classification Search
USPC .............................................. 433/27; 600/301
See application file for complete search history.

(56) References Cited

U.S. PATENT DOCUMENTS

| | | |
|---|---|---|
| 6,754,516 B2 | 6/2004 | Mannheimer |
| 7,123,950 B2 | 10/2006 | Mannheimer |
| 7,639,145 B2 | 12/2009 | Lawson et al. |
| 7,962,188 B2 | 6/2011 | Kiani et al. |
| 8,203,438 B2 | 6/2012 | Kiani et al. |
| 8,400,290 B2 | 3/2013 | Baker |
| 8,401,606 B2 | 3/2013 | Mannheimer |
| 8,401,607 B2 | 3/2013 | Mannheimer |
| 8,456,295 B2 | 6/2013 | Rantala |
| 8,547,209 B2 | 10/2013 | Kiani et al. |
| 8,622,902 B2 | 1/2014 | Woehrle |

(Continued)

*Primary Examiner* — Nicole F Lavert
(74) *Attorney, Agent, or Firm* — Shook, Hardy & Bacon L.L.P.

(57) ABSTRACT

Systems and methods are provided for evaluating an alarm condition for a monitored patient in a population of one or more patients. One or more physiological parameters pertaining to the patient, or physiological variables, are used to form a time series describing the patient status. A quantile threshold is determined for a patient. A monitor is initialized and begins generating a binary raw alarm signal. The binary signal is filtered with a low pass filter, and the filtered data is subjected to a quantile operation to determine if a particular sample exceeds the determined quantile threshold. If the quantile threshold is exceeded, then a check is performed to see if the raw binary alarm signal also indicates an alarm. If both the preliminary alarm indication and the raw binary signal indicate an alarm, then an alarm is emitted; otherwise monitoring continues.

17 Claims, 8 Drawing Sheets

(56) References Cited

U.S. PATENT DOCUMENTS

| | | | |
|---|---|---|---|
| 2002/0077536 A1* | 6/2002 | Diab | A61B 5/14546 600/323 |
| 2004/0243659 A1* | 12/2004 | Nikitin | G06G 7/02 708/819 |
| 2010/0076514 A1* | 3/2010 | Cho | A61B 5/0031 607/18 |
| 2014/0096146 A1* | 4/2014 | Maor | G06F 11/3419 719/318 |
| 2014/0313030 A1* | 10/2014 | Ten Kate | A61B 5/1115 340/539.12 |

* cited by examiner

SpO2 Example: FIR Statistical Performance, Q=0.90

| | TRUE POSITIVE | TRUE NEGATIVE |
|---|---|---|
| POSITIVE | 100 | 18 |
| NEGATIVE | 0 | 882 |

*FIG. 6A.*

SpO2 Example: 8$^{th}$-Order Chebyshev Type-II Statistical Performance, Q=90

| | TRUE POSITIVE | TRUE NEGATIVE |
|---|---|---|
| POSITIVE | 100 | 3 |
| NEGATIVE | 0 | 897 |

*FIG. 6B.*

```
###############################################################

# digital low-pass filtering of monitor alarm time series

######################################################### library(signal)

construct an 8th-order Chebyshev Type-II low-pass filter:
ch <- cheby2(n=8, Rp=30, W=0.075, type="low")
# group delay as a function of frequency
#   grpdelay(ch, Fs=100)
# spectrum
#   freqz(ch, Fs=100)

# apply the filter to signal
t <- seq(0, 255, by=1)              # 256-sec sample, Fs = 1 Hz
x <- unlist(read.csv(file="c:/0_cerdsm/IP/CEP_FIR/dsm_alarm01.csv"))
z <- filter(ch, x)

# threshold at 90th percentile
tail <- 0.90
z <- 1*(abs(z) > quantile(abs(z),probs=tail))

# compare to 15-sec delay, boxcar avg with threshold
y <- unlist(read.csv(file="c:/0_cerdsm/IP/CEP_FIR/dsm_alarm02.csv"))

# plot the original time series with 15-sec boxcar-avg and Chebyshev
plot(t, x, type="l", lwd=2)
lines(t, y, col="red", lwd=2)
lines(t, z, col="green", lwd=2)

# construct and apply 8-sample FIR filter
z <- fftfilt(rep(1, 8)/8, x)

# threshold at 90th percentile
tail <- 0.90
z <- 1*(abs(z) > quantile(abs(z),probs=tail))

# plot the original time seris with 15-sec boxcar-avg and FIR
plot(t, x, type="l", lwd=2)
lines(t, y, col="red", lwd=2)
lines(t, z, col="green", lwd=2)
```

*FIG. 7.*

STREAM-BASED ALARM FILTERING

CROSS-REFERENCE TO RELATED APPLICATIONS

This application claims the benefit of U.S. Provisional Application No. 61/981,015, titled "STREAM-BASED ALARM FILTERING," filed on Apr. 17, 2014; which is hereby expressly incorporated by reference in its entirety.

INTRODUCTION

When a patient's clinical condition is deemed sufficiently abnormal, a number of devices or technologies are provided by medical staff to continuously monitor patient physiology. This allows bedside staff to check patient condition by observing physiological measures such as temperature, blood pressure, respiration rate, blood oxygen saturation, pulse rate, and other vital signs or variables. A dangerously high or low value of a measure alerts staff to investigate causes and potential interventions to alleviate imminent ill-effects of an extreme physiological value.

Unfortunately, for a given patient, staff may not be at bedside observing the complete physiological picture when a physiological measure approaches a dangerous level. For this reason, a device or technology that measures a physiological level may use an alarm threshold so that if the physiological measure is above or below the alarm threshold, an alarm tone or other form of notification is emitted to draw attention to the level indicated by the device or technology, and perhaps also to summon staff to the bedside.

Multiple problems are created by poor physiological measures. Too often, alarms, which can include notifications, are presented to a clinician when a measurement is out of bounds relative to a threshold, but the underlying physiological indicator for the monitored patient is not a concern for a well-informed clinician. For example, the physiological measure for a particular patient may be abnormal, but typical for this patient, and stable; the physiological measure is out of bounds because a procedure is being performed, or because a probe has lost its source of signal, or because a probe is experiencing an error condition unrelated to patient physiology, etc. Such errant alarms effectively "train" clinicians that most alarms are a nuisance, e.g., a message that the device measuring a physiological parameter needs to be attended to, effectively distracting the clinician to focus on a device rather than on patient care. Often, as a result, alarms are disabled, thresholds are widened to lessen the frequency of alarms, and legitimate alarms are ignored. Clinicians become desensitized to alarms, safety is eroded, and adverse outcomes increase. There is a general continuing need for improving physiological signal processing in support of clinical observation and decision making, so that false alarms are reduced, sensitivity to adverse physiology is increased, appropriate responses are aided, and inappropriate requests are made less frequently.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter. The present invention is defined by the claims.

Systems, methods, and computer-readable media are provided for processing one or more physiological measurements or other physiological variables for clinical decision making. For example, an embodiment determines that an alarm condition or a maintenance condition is present for a given patient. One or more physiological variables such as blood oxygen saturation level, a respiration rate, an Electro-Encephalogram (EEG) signal, other vital signs, a biomarker(s), or an optical image of the patient are monitored to form a time series of the one or more physiological variable values.

An embodiment is directed to a method for collecting and analyzing data to assess the physiologic status and health of human and/or animal subjects. An embodiment incorporates methods from the fields of digital signal processing (DSP) and spectral analysis of a time series signal to low-pass filter a time series of binary alarm signals emanating from a physiologic monitor. An embodiment is to be used in conjunction with monitoring devices' alarm thresholds for the purpose of reducing the rate of false-alarms emission. Additionally, in an embodiment, a filtered binary signal represents a new predictive and classificatory biomarker in its own right and may be used as a basis for (a) asserting alarm conditions worthy of human diagnostic, therapeutic, or preventive intervention or (b) predicting the imminent emergence of such alarm conditions in the near future.

BRIEF DESCRIPTION OF THE DRAWINGS

The present invention is described in detail below with reference to the attached drawing figures, wherein:

FIGS. 6A and 6B depict tables showing the statistical performance of the embodiments for an example case; and FIG. 7 illustratively provides an example embodiment of a computer program routine for determining and applying FIR and 8th-Order Chebyshev filter to the alarm data, in accordance with an embodiment of the invention.

DETAILED DESCRIPTION

Figure 1A:
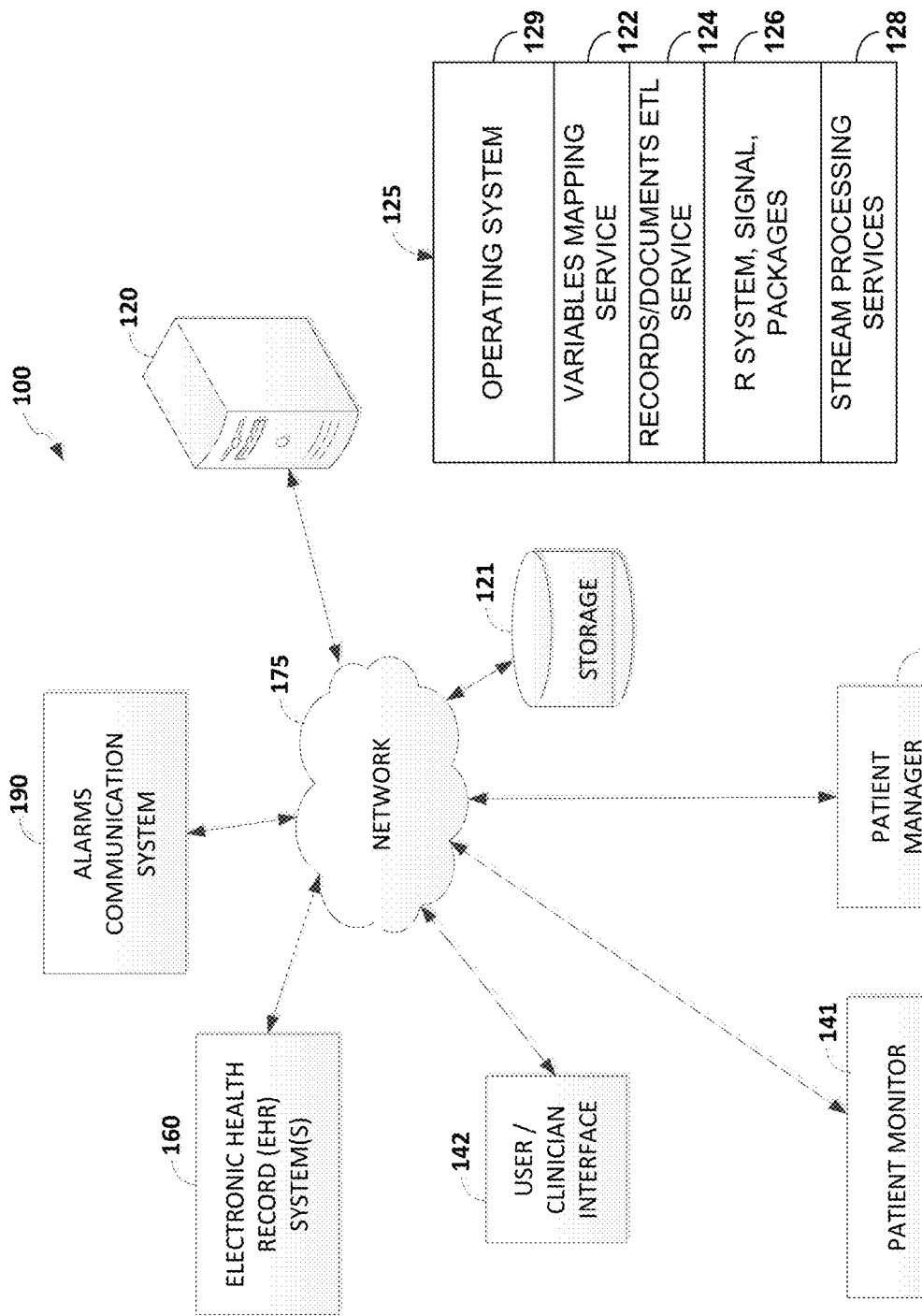
FIGS. 1A-1B depict aspects of an operating environment suitable for practicing an embodiment of the invention.

The subject matter of the present invention is described with specificity herein to meet statutory requirements. However, the description itself is not intended to limit the scope of this patent. Rather, the inventor has contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of the invention may be embodied as, among other things, a method, system, or set of instructions embodied on one or more computer-readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer-readable media.

Computer-readable media include both volatile and nonvolatile media, removable and nonremovable media, and contemplate media readable by a database, a switch, and various other network devices. By way of example, and not limitation, computer-readable media comprise media implemented in any method or technology for storing information, including computer storage media and communications media. Examples of stored information include computer-useable instructions, data structures, program modules, and other data representations. Computer storage media examples include, but are not limited to, information-delivery media, RAM, ROM, EEPROM, flash memory or other memory technology, CD-ROM, digital versatile discs (DVDs), holographic media or other optical disc storage, magnetic cassettes, magnetic tape, magnetic disk storage, other magnetic storage devices, and other computer hardware or storage devices. These technologies can store data momentarily, temporarily, or permanently.

Clinicians in modern acute-care health institutions may be exposed to hundreds of physiologic monitor alarms per patient per day. Monitor alarms are intended to alert clinicians to conditions that may result in harm to the patient. However, when a clinician is faced with an excessive number and frequency of alarms, the disruption and distraction may be so great as to produce so-called "alarm fatigue," leading the clinician to disregard many of the alarms. This, in turn, gives rise to inferior outcomes, owing to errors of omission and commission.

The problem of alarm hazards is of increasing interest. Such hazards include alarm fatigue and nonresponse, clinically unjustified or inappropriate alteration of alarm settings so as to silence or reduce the frequency of alarm-emission, modifying alarms temporarily without later restoring them to original settings when the circumstances that justified the temporary change have abated, and improper or untimely communication of alarm signals to staff members caring for the patient.

Typically, medical device monitors are functionally attached to patients whose clinical condition is sufficiently abnormal as to require such monitoring. As such, true-alarm conditions arise with considerable frequency, often dozens of times per patient per day. Physiologic monitoring devices and their associated alarm thresholds may be designed for high sensitivity, to have a low false-negative rate and to not miss true-alarm events. Concomitantly, a large number of false-alarm conditions also arise each day, resulting in alarms that summon clinicians, in the case when there is no physiological crisis. In addition to high sensitivity, if monitor parameter thresholds are set too tight, true but clinically insignificant alarms arise, known as "nuisance alarms." When alarms are deemed to be "nuisances" (having no clinical import), the clinicians tend to disable, silence, or ignore the alarm warnings. Rather than promoting safety, the net result is to desensitize the users, eroding safety and causing adverse outcomes, such as injury or even death.

False-positive alarm rates and nuisance alarm rates in a clinical setting can be well above 50%. Such high false alarm rates have a negative impact on the clinical decision-making process. Other attempts to minimize false alarms and nuisance alarms have been unsatisfactory in some respects.

An embodiment is directed to a system and method for optimizing physiologic monitoring of a subject, comprising longitudinally measuring one or more physiologic biomarkers; constructing a time series from binary alarm signals emitted from monitor devices that perform said measurements; applying a low-pass digital filter to the resulting transformed time series; dynamically and adaptively dichotomizing the filtered time series via a quantile threshold; and, if the last sample of the filtered time series has a status equal to 1 indicating "alarm," permitting the filtered alarm to be propagated or emitted to notify appropriate clinical personnel.

An embodiment is directed to methods and devices for collecting and analyzing data to assess the physiologic status and health of human and/or animal subjects. An embodiment incorporates methods from the fields of digital signal processing (DSP) and spectral analysis of a time series signal to low-pass filter a time series of binary alarm signals emanating from a physiologic monitor. The system and method is intended to be used in conjunction with monitoring devices' alarm thresholds for the purpose of reducing the rate of false-alarms emission. Additionally, a resulting statistic represents a new predictive and classificatory biomarker in its own right and may be used as a basis for (a) asserting alarm conditions worthy of human diagnostic, therapeutic, or preventive intervention or (b) predicting the imminent emergence of such alarm conditions in the near future.

An embodiment enables reliable determination of true-positive versus false-positive alarms, substantially reducing so-called "alarm fatigue" associated with the emission of false alarms. This may provide a more effective means of mitigating health risks associated with excessive false alarming, compared to other efforts that rely solely on time series analysis or simple threshold transgression.

An alarm generation system should provide decision input criteria that allow the system to detect a very high fraction of life-threatening situations that require prompt attention (should have a low false-negative rate). Additionally, an alarm generation system should ascertain dangerous situations quickly. Further, an alarm generation system should have a very low rate of false-positives (indicating a hazard when none exists). In other words, the statistical sensitivity and specificity should both be as high as possible, preferably close to 100%. Beyond this, some monitoring device alarms may have one or more of the following goals: (1) suppression of alarm emission in situations that are not threatening or whose severity does not require prompt attention; (2) diagnostic and classificatory alarms denoting a pattern or predicate that merits a particular type of therapeutic attention or intervention, as opposed to merely disclosing an out-of-range condition; and (3) detection of sensor or device malfunction, so that appropriate maintenance or corrective action can be undertaken to restore accurate and physiologically valid sensor measurements.

Some efforts attempt to decrease false-positive alarms and increase the statistical positive predictive value (PPV) of alarms that are emitted by physiological monitoring systems. Alarm filtering that is based on a time integral or area-under-the-curve (AUC) for persistent excursions of a physiologic signal outside of the alarm threshold provide some benefit insofar as transient threshold transgressions often do tend to self-correct. Adding short delays of up to about 120 seconds may significantly decrease the number of false-positive alarms. Some approaches may use signal morphology, timing differences, cross-correlation between two or more signals, signal rate-of-change, or signal-to-noise ratio or other signal quality metrics to improve alarm accuracy.

Other attempts or efforts at decreasing false alarm conditions are deficient due to:

(1) Excessive false-positive "false-alarm" rate, especially for hypoxia/desaturation or bradycardia or tachycardia or ventricular fibrillation;

(2) Excessive false-negative rate, especially for ventricular tachycardia and similar conditions;

(3) Delays of up to 120 seconds or more after threshold transgression when a signal is longitudinally observed or summed (AUC) to determine whether persistence of the signal's abnormal out-of-bounds state qualifies for notifying the clinician of the alarm conditions;

(4) Arbitrary factory-preset default alarm thresholds that are not context-sensitive to the particular attributes and physiological variable time series distribution or frequency-domain power spectrum of signals arising in a particular patient or population of patients;

(5) Proneness to arbitrary resetting of user-adjustable thresholds, so as to silence alarms or reduce the rate or likelihood of alarms being emitted. Doing this generally entails arbitrarily permitting commensurate increase in a false-negative rate, suppressing true alarm conditions warranting attention, and preventive/corrective action;

(6) Necessity of using multivariate signals that relate to two or more physiological variables, often from two or more sensors, which may entail extra expense, and involve difficulties assuring non-skewed time coordinates from the data-feeds from multiple data acquisition systems;

(7) Process complexity that entails extra preparation and ongoing work for the clinician and a higher level of training required for the clinician to use the system properly;

(8) Process complexity involving k-nearest neighbor (k-NN), support vector machine (SVM), neural network, Bayesian, or other clustering and decision-tree induction algorithms to establish thresholds and methods for discriminating "normal" from "abnormal" alarm-worthy states;

(9) Static control-limit thresholds and algorithms, such that individualization to particular disease-states or personalization to particular patients is not practical;

(10) The need for a user to know the patient's diagnoses or clinical context and be able at the outset to select exactly one diagnosis or context descriptor that best characterizes the population to which the relevant control-limits or algorithms or alarm thresholds are to be localized. Frequently patients have multiple concurrent/comorbid diagnoses, such that selecting one context diagnosis is difficult or invalid to do, since there are several that would simultaneously be applicable. But if a combination of conditions is chosen as a baseline, there may not be sufficient prior data to guide threshold estimation or selection. Other patients who have not yet received a diagnosis or diagnoses established at other health institutions are not available or known to the user, such that selecting an alarm-localizing diagnosis is not possible at the time that measurements and physiologic monitoring commence; and

(11) Lack of automatic adaptation to the longitudinally evolving context or physiologic condition of the patient, so that patient diagnosis must be changed or updated with the passage of time.

An embodiment establishes a method for ameliorating these limitations and provides objective, quantitative means for automatically discriminating true-positive versus false-positive alarm conditions in near real time, to enable filtering and censoring of false-positive alarms while permitting true-positive alarms to be promptly emitted without delay.

In an embodiment, the determination that an alarm should be emitted comprises:

1. Assembling a finite-width, moving-window time series sample of the raw alarm status for the current period plus recent periods.

2. Applying a digital filter to the time series.

3. Performing a dichotomization by calculating whether or not at least one element in the filtered time series exceeds a selected quantile threshold Q, such as 90%. If an element exceeds the quantile threshold Q, then a preliminary alarm condition is indicated.

4. If the last raw sample on which the dichotomized filtered time series has a status equal to 1 denoting "alarm," then the preliminary alarm condition is deemed to be a true-positive alarm and an alarm is emitted. If the last raw sample status is 0 denoting "no alarm," then the preliminary alarm condition is deemed not to represent a true-positive alarm and no alarm is emitted.

In an alternative embodiment of 4, if the last sample in the dichotomized filtered time series has a status equal to 1 denoting "alarm," then the condition is deemed to be a true-positive and an alarm is emitted. If the last status is 0 denoting "no alarm," then the condition is deemed not to represent a true-positive alarm and no alarm is emitted.

In an embodiment, a moving window of the time series comprises K time windows of N values each. A quantile fraction Q represents the fraction of resultant filtered values to effectively discard. The N*K values in the filtered time series are then sorted by filtered value to determine a rank order statistic. For example, a rank order statistic could be the largest value VL in the lower value quantile of the Q*N*K values. In an embodiment, the largest (1−Q)*N*K+1 values are found out of the available N*K values and the smallest of these values is determined to have value VL. In an embodiment, if the present value of the filtered time series is greater than VL, then a preliminary alarm condition is determined. In an embodiment, the comparison is greater than or equal to VL. If in the presence of a preliminary alarm condition the most recent value of the raw alarm time series has a status equal to 1, or a raw alarm condition, then an alarm condition is emitted. Otherwise, new raw alarm data is accumulated and the process of alarm evaluation repeats for the updated data set. In an embodiment, the window of processed values changes for each sample of new data, and the N*K values considered changes by one sample, adding a single sample and deleting the oldest sample in the moving window. In an embodiment, new data is processed by deleting a set of N values and adding a more recent set of N values. In an embodiment, VL is computed with each new sample. In an embodiment, VL is determined only every N samples.

In an embodiment, the fraction Q is determined based on an input selection table that is stored in a software configuration database. In an embodiment, Q is determined based on a number of factors dependent upon patient data such as measured heart rate, respiratory rate, blood pressure, oximetry data, or their processed values such as trends, averages, or rank order statistic results. In an embodiment, a number of factors are combined through a weighted combination of factors to determine a resultant Q value for a patient. In an embodiment, if the Q value for oximetry data is being determined, a patient's oximitry data is weighted heavily while the patient's heart rate and respiratory rate are weighted relatively less, and blood pressure is weighted even lower. In an embodiment, Q is determined for a particular patient based on clinician input. In an embodiment, a clinician defines a pie chart assignment representing the fractional $R_i$ of likely valid alarms assigned to patient i in a population of M patients, so that the sum $R_1 + \ldots + R_i + \ldots R_M = 1$. Patient i is then assigned quantile $Q = (1 - R_i)$. In an embodiment, criticality $C_i$ is chosen to be equal to the fractional likelihood $R_i$. In an embodiment, a patient's quantile threshold is chosen based on a product of $C_i$ and $R_i$, e.g., $Q = (1 - R_i * C_i)$. In an embodiment, the clinician selects a proportional fraction assigned to each patient according to whether or not alarm service is expected for that patient, so that resources are intentionally allocated by the clinician based on planned resource needs. In an embodiment, the quantile assigned to a patient is a function of an equally weighted quantile. In an embodiment, the quantile assigned to a patient is determined based on beneficial alarm loads that can be processed by a resource pool of available attendants. In an embodiment, the quantile chosen for a patient is determined based on likely criticality of an alarm based on patient history. For example, a patient's criticality could decrease exponentially from a time at the beginning of post-operation time to a future time, such as an expected substantial recovery time, by following a suitable time constant of decay. In an embodiment, the value of an exponential time constant of criticality is chosen to be a multiple of the expected recovery time (or alternatively to a time that places criticality below 0.2 at a time equal to about twice the recovery time). In an embodiment criticality varies linearly between expected endpoints. In an embodiment any patient's selected or computed quantile threshold is subject to a maximum limit value, e.g. a maximum of 80%.

An embodiment automatically personalizes an alarm for monitored pulse oximetry. A series of patient pulse oximetry data was acquired, taken from fingertip plethysmographic $SpO_2$ data provisioned with a 0.5 Hz sampling rate and ±1% precision and accuracy. Recorders were randomly selected from a patient health records data warehouse, which is derived from Cerner electronic health record (EHR) from 100% of episodes of care that are incident upon the participating health institutions. The personally identifiable information was removed in conformance with U.S. HIPAA law and regulations, and the de-identified data were stored in a separate, secure database. An embodiment using an 8th-Order Chebyschev Type-II filter was able to identify positive alarm signals with 100% sensitivity and 99% or greater specificity. The false-positive false-alarm rate in the derivation cohort was 2.9%, a 95% reduction compared to the historical control cohort (48%, $p<0.001$) with the lower alarm limit set at $SpO2=89\%$. The false-negative true-alarm suppression rate was 0%.

Turning now to FIG. 1A, there is presented an example operating environment 100 suitable for practicing an embodiment. Example operating environment 100 includes a computerized system for compiling and/or running an embodiment of an information architecture that performs decision support recommendation service. With reference to FIG. 1A, an electronic health record (EHR) system, such as hospital EHR system 160, is communicatively coupled to network 175, which is communicatively coupled to computer system 120. In an embodiment, components of operating environment 100 that are shown as distinct components may be embodied as part of or within other components of environment 100. For example, an EHR system 160 may be implemented in computer system 120. Similarly, a single EHR system may perform functions for one or more remote EHR systems (not shown).

In an embodiment, network 175 includes the Internet and/or one or more public networks, private networks, other communications networks such as a cellular network, or similar network(s) for facilitating communication among devices connected through the network. Network 175 may be determined based on factors such as the source and destination of the information communicated over network 175, the path between the source and destination, or the nature of the information. For example, intra-organization or internal communication may use a private network or virtual private network (VPN). Moreover, in some embodiments, items shown communicatively coupled to network 175 may be directly communicatively coupled to other items shown communicatively coupled to network 175.

In an embodiment, operating environment 100 may include a firewall (not shown) between a first component and network 175. In such an embodiment, the firewall may reside on a second component located between the first component and network 175, such as on a server (not shown), or reside on another component within network 175, or may reside on or as part of the first component.

An embodiment of electronic health record (EHR) system 160 includes one or more data stores of health records, which may be stored on storage 121, and may further include one or more computers or servers that facilitate the storing and retrieval of the health records. In an embodiment, an EHR system 160 is implemented as a cloud-based platform or is distributed across multiple physical locations. EHR system 160 may further include record systems, which store real-time or near-real-time patient (or user) information, such as wearable, bedside, or in-home patient monitors, for example.

Although FIG. 1A depicts an exemplary EHR system, it is contemplated that an embodiment relies on user manager 140 and/or monitor 141 for storing and retrieving patient record information such as information acquired from monitor 141.

Example operating environment 100 further includes provider clinician interface 142 communicatively coupled to an EHR system 160. Although environment 100 depicts an indirect communicative coupling between interface 142 and EHR system 160 through network 175, it is contemplated that an embodiment of interface 142 is communicatively coupled to EHR system 160 directly. An embodiment of interface 142 takes the form of a user interface operated by a software application or set of applications on a client computing device such as a personal computer, laptop, smartphone, or tablet computing device. In an embodiment, the application includes the PowerChart® software manufactured by Cerner Corporation. In an embodiment, the application is a Web-based application or applet. A provider clinician application facilitates accessing and receiving information from a user or health care provider about a specific patient or set of patients for which sleep architecture characterization is to be performed and facilitates the display of results, recommendations, or orders, for example. In an embodiment, interface 142 also facilitates receiving orders for the patient from the clinician/user, based on the results of monitoring. Interface 142 may be used for providing diagnostic services, such as evaluating information as discussed in connection to FIG. 3.

Example operating environment 100 further includes computer system 120, which may take the form of a server, which is communicatively coupled through network 175 to EHR system 160, storage 121, and patient manager 140.

In an embodiment, EHR system 160 is a workstation that receives an alarm indication from patient manager 140 and performs analysis processing to determine whether or not to emit an alarm indication. In an embodiment, EHR system 160 comprises an electronic display that presents an alarm indication to a clinician. In an embodiment, EHR system 160 emits an alarm by sending a notice via alarms communication system 190 to clinicians carrying compatible personal communication devices. In an embodiment, a personal communication device is a computer, a pager, a laptop computer, a computer workstation, a desktop computer, a tablet, a wired telephone, a wireless telephone, cellular telephone, personal digital assistant, or smartphone. In an embodiment, a communication alarm system provides a short message service (SMS) message, email, audible tone, audible announcement, or a display warning.

An embodiment of patient manager 140 takes the form of a user interface and application, which may be embodied as a software application operating on one or more mobile computing devices, tablets, smartphones, front-end terminals in communication with back-end computing systems, laptops, or other computing devices. In an embodiment, manager 140 includes a Web-based application or set of applications usable to manage user services provided by an embodiment of the invention. For example, in an embodiment, manager 140 facilitates processing, interpreting, accessing, storing, retrieving, and communicating information acquired from monitor 141. In an embodiment, manager 140 sends an alarm indication directly to clinician interface 142 through a direct connection. In an embodiment, manger 140 sends an alarm indication via network 175 to provider clinician interface 142. In an embodiment, manager 140 sends a maintenance indication to provider clinician interface 142. Similarly, a clinician is provided alarm or maintenance information by patient manager 140 or from a monitor (e.g., monitor 141, 143, 144, 145, 146, 147, 148, or 149). Moreover, in an embodiment of manager 140, an interface component may be used to facilitate access by a user to functions or information on monitor 141, such as operational settings or parameters, user identification, user data stored on monitor 141, and diagnostic services or firmware updates for monitor 141, for example.

As shown in example environment 100, manager 140 in an embodiment is communicatively coupled to monitor 141 and to network 175. In an embodiment, patient monitor 141 communicates via network 175 to computer 120 and/or provider clinician interface 142. An embodiment of monitor 141 comprises one or more sensor components operable to acquire biometric information about a patient, such as information associated with a particular physical or mental state of the user, and which may be acquired periodically or as one or more time series. In an embodiment, monitor 141 comprises a sensor or probe component operable for sensing a patient's temporal activity, such as sensing EEG signals derived from a patient.

Figure 2:
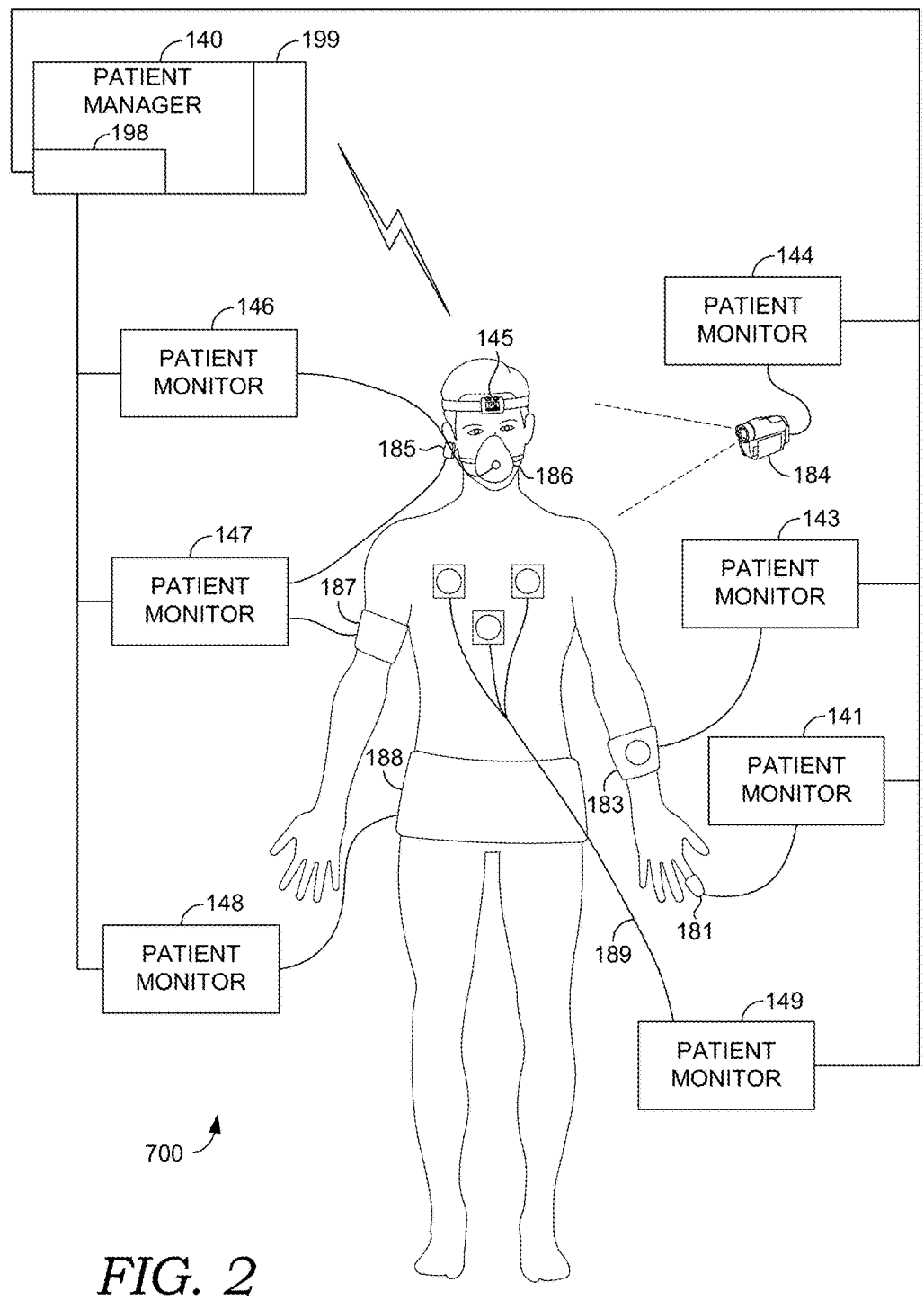
FIG. 2 depicts aspects of an operating environment suitable for practicing an embodiment of the invention.

Turning briefly to FIG. 2, patient physiological variable context diagram 700 illustrates a number of patient monitors (141, 143, 144, 145, 146, 147, 148, and 149) for sensing various types of physiological measurements or physiological variables. A monitor such as 145 may monitor muscle activity which might be sensed from electromyogram signals, eye movement which might be sensed from electro-oculogram signals, or other biometric information. In an embodiment, a monitor such as 145 simply consists of a sensor probe, such as an EEG probe, and a communication link that periodically transmits identification information and probe data to a network interface 199 on a computer such as patient manager 140, so that the time series of monitored values is stored on patient manager 140, enabling the patient manager to form a raw binary alarm indication and/or a physiological variable decision statistic. In an embodiment, patient monitor 144 collects raw sensor information, such as optical sensor 184, and performs signal processing, such as movement detection, kinematic modeling, distance and shape processing, velocity measurement, forming a physiological variable decision statistic, cumulative summing, trending, wavelet processing, thresholding, computational processing of decision statistics, logical processing of decision statistics, etc. In an embodiment, a monitor, such as patient monitor 149, 148, 147, 146, 144, 143, or 141, communicates with a patient manager 140 through wired or wireless network interface 198, thus allowing patient manager 140 to perform multi-sensor or single-sensor processing. In an embodiment, patient manager 140 performs aggregate processing of multiple probe sources to create a single binary patient alarm signal. In an embodiment, a monitor such as 141 makes use of a fingertip oximetry probe 181 to collect data that alarms on condition of hypotaxia/desaturation. In an embodiment, patient monitor 141 sends a binary alarm signal to patient manager 140. In an embodiment, monitor 147 makes use of a first physiological variable probe such as pressure cuff 187 and a second physiological variable probe such as earlobe oximetry probe 185. Probe 187 is useful for irregularities in blood pressure such as unusually high or low mean arterial pressure, diastolic pressure, or systolic pressure. Though monitor 147 is shown with two probe types, an embodiment of monitor 147 has an arbitrarily large number of probes for the same physiological variable or for many physiological variables. In an embodiment, monitor 149 makes use of multi-sensor electrocardiogram probe 189. Probe 189 is useful for simultaneously measuring electrical activity of the heart and respiration rate for detection of bradycardia, tachycardia, ventricular fibrillation, etc. In an embodiment, probe 189 is used to detect respiration rate redundantly over three pairs of electrodes, allowing monitor 149 to collect data for detection of hyperventilation, hypoventilation, etc. An embodiment of a probe such as probe 189 monitors one or more of Pulmonary Capilary Web Pressure (PCWP), Left Atrium Pressure (LAP), Central Venous Pressure (CVP), Intra Cranial Pressure (ICP), Central Venous Oxygen Saturation (SCVO2), Hemoglobin Oxygen Saturation (SO2), Arterial Oxygen Saturation (SpO2), temperature, blood pressure, rate, temperature, or other physiological variable. An embodiment of monitor 148 tracks contractions and in-utero baby heart rate for a female subject during labor using cardiotocometer probe 188. An embodiment of probe 188 monitors two patients who are linked, e.g., during birth or in a transplant operation. An embodiment of monitor 146 tracks respiration directly through respiration probe 186. An embodiment of monitor 143 tracks temperature with surface temperature probe 183.

In an embodiment, one or more sensor components of monitor 145 may comprise a user-wearable sensor component or sensor component integrated into the user's or patient's living environment. Examples of sensor components of monitor 145 include a sensor positioned on an appendage (on or near the user's head, attached to the user's clothing, worn around the user's head, neck, leg, arm, wrist, ankle, finger, etc.); skin-patch sensor; ingestible or subdermal sensor; sensor component(s) integrated into the user's living environment (including the bed, pillow, or bathroom); and sensors operable with or through a smartphone carried by the user, for example.

An embodiment of monitor 141 stores user-derived data locally or communicates data over network 175 to be stored remotely. In an embodiment, manager 140 is wirelessly communicatively coupled to monitor 145. Manager 140 may also be embodied as a software application or app operating on a user's mobile device. In an embodiment, manager 140 and monitor 141 are functional components of the same device, such as a device comprising a sensor and a user interface. In an embodiment, manager 140 is embodied as a base station, which may also include functionality for charging monitor 141 or downloading information from monitor 141.

Additionally, an embodiment of monitor 145 shown in FIG. 2 includes some functionality of manager 140. For example, an embodiment of monitor 145 includes a user interface with functionality for configuring operational settings, such as on and off, or settings for storing and/or communicating sleep-related information acquired from the user information, such as uploading the information to manager 140 or to storage 121, and display functionality for viewing or reviewing physiological variable information acquired from a patient. In an embodiment, a clinician interface is presented on monitor 141 showing an indication of a raw alarm condition. In an embodiment, monitor 141 receives a current threshold setting for generating a binary alarm signal from a patient manager 140 based on an alarm management strategy contained in a configuration file, or determined by a clinician. An embodiment of a local indication flashes an indication that raw binary alarm data has been sent to a patient manager, such as patient manager 140, without presenting an unsettling tone or visual warning. In one embodiment, monitor 145 is embodied as a Zeo sleep sensor headband manufactured by Zeo Inc. of Newton, Mass.

With reference to FIG. 1A, an embodiment of monitor 141 includes analog-to-digital (A/D) converters for converting analog-acquired information into digital information. For example, in one embodiment, user information is acquired at 512 samples per second. Because sleeping-related signals include low frequencies in comparison to other biological signals, an appropriate sampling rate is determined to adequately capture information sufficient to characterize a user's sleep architecture. For example, Delta or Theta cycles have comparatively low frequencies.

In an embodiment, monitor 141 includes functionality for processing user-derived information locally or for communicating the information to computer system 120 or manager 140, where it may be processed. In an embodiment, the processing may be carried out or facilitated by one or more software agents, as described below. In an embodiment, the processing functionality, which may occur on monitor 141, manager 140, and/or computer system 120, includes signal conditioning, such as removing noise or erroneous information. In an embodiment, processing functionality is operable to process user-derived information, such as EEG waveform data, as it is acquired, continuously or periodically such as every 10, 15, 30, or 60 seconds or every few minutes. In an embodiment, the processing includes classifying the user-derived information acquired for a particular time interval into a category. For example, in an embodiment, monitor 145 samples a user's EEG information and processes (or communicates to manager 140 or computer system 120 for processing) the information approximately every time interval to classify the user's state for that time interval. For example, every 30-second time interval, the user's sleeping state may be determined to be one of stage 1, stage 2, etc., theta, delta, etc., or awake, light sleep, REM sleep, deep sleep, or undetermined. Furthermore, in an embodiment, processing further includes determining a sleep score or sleep number, which qualifies the sleep state. In an embodiment, this sleep score is based on the number of time intervals occurring within the sleep categories for a user over a night. In an embodiment of monitor 145 comprising a Zeo sleep sensor device, described above in connection to FIG. 2, some models of the Zeo device include functionality for determining a number quantifying the user's sleep based on total sleeping time, and time spent in various sleep states, which is referred to as a ZQ (for Zeo Quotient).

Computer system 120 comprises one or more processors operable to receive instructions and process them accordingly, and may be embodied as a single computing device or multiple computing devices communicatively coupled to each other. In an embodiment, processing actions performed by system 120 are distributed among multiple locations such as one or more local clients and one or more remote servers. In an embodiment, system 120 comprises one or more computing devices, such as a server, desktop computer, laptop, or tablet, cloud-computing device or distributed computing architecture, a portable computing device such as a laptop, tablet, ultra-mobile P.C., or a mobile phone.

An embodiment of computer system 120 includes computer software stack 125, which in some embodiments operates in the cloud, as a distributed system on a virtualization layer within computer system 120. An embodiment of software stack 125 includes operating system 129. Operating system 129 may be implemented as a platform in the cloud. Operating system 129 is capable of hosting a number of services such as 122, 124, 126, and 128. An embodiment of services 122, 124, 126, and 128 run as a local or distributed stack in the cloud, on one or more personal computers or servers such as system 120, and/or a computing device running manager 140. In an embodiment, manager 140 operates in conjunction with software stack 125.

In an embodiment, variables indexing service 122 and records/documents ETL service 124 provide services that facilitate retrieving frequent item sets, extracting database records, and cleaning the values of variables in records. For example, variables mapping service 122 may perform functions for synonymic discovery, indexing or mapping variables in records, or mapping disparate health systems' ontologies, such as determining that a particular medication frequency of a first record system is the same as another record system. In an embodiment mapping service 122 provides service that facilitates retrieving frequent item sets, extracting database records, and cleaning values of variables in records. In an embodiment, these services may invoke software services 126. Software services 126 perform statistical software operations, and include statistical calculation packages such as, in an embodiment, the R system (the R-project for Statistical Computing, which supports R-packages or modules tailored for specific statistical operations, and which is accessible through the Comprehensive R Archive Network (CRAN) at http://cran.r-project.org); R-system modules or packages including tsDyn or similar services for facilitating implementation of nonlinear autoregressive time series models, pracma for performing practical numerical mathematical functions, psd for estimating the power spectral density, wavelets for computing wavelets, strucchange for testing monitoring and dating structural change, tseriesChaos for nonlinear time series operations, arulesSequences or similar services for facilitating operations such as K-nearest neighbor distance calculations, SIGNAL or similar services such as MATLAB, for performing signal processing functions such as performing digital synthesis of digital filters such as butterworth, chebyshev, elliptical, finite impulse response filter, infinite impulse response, and savitzky-golay filters and quantreg for computing quantile regression and related methods such as kuantile and quantile. Software packages 126 are associated with services 128, which include IBM infosphere stream processing services, Apache Hadoop and Hbase framework, or similar frameworks operable for providing a distributed file system, and which in some embodiments facilitate or provide access to cloud-based services such as those provided by Cerner Healthe Intent®.

Example operating environment 100 also includes storage (or data store) 121, which in some embodiments includes patient data for a candidate patient and information for multiple patients; variables associated with patient recommendations; recommendation knowledge base; recommendation rules; recommendations; recommendation update statistics; an operational data store, which stores events, frequent itemsets (such as "X often happens with Y", for example), and item sets index information; association rulebases; agent libraries, solvers and solver libraries, and other similar information including data and computer-usable instructions; patient-derived data; and health-care provider information, for example. It is contemplated that the term data includes any information that can be stored in a computer-storage device or system, such as user-derived data, computer usable instructions, software applications, or other information. In an embodiment, data store 121 comprises the data stores associated with the one or more EHR systems, such as 160 and patient manager 140. Further, although depicted as a single storage data store, data store 121 may comprise one or more data stores, or may be in the cloud.

Figure 1B:
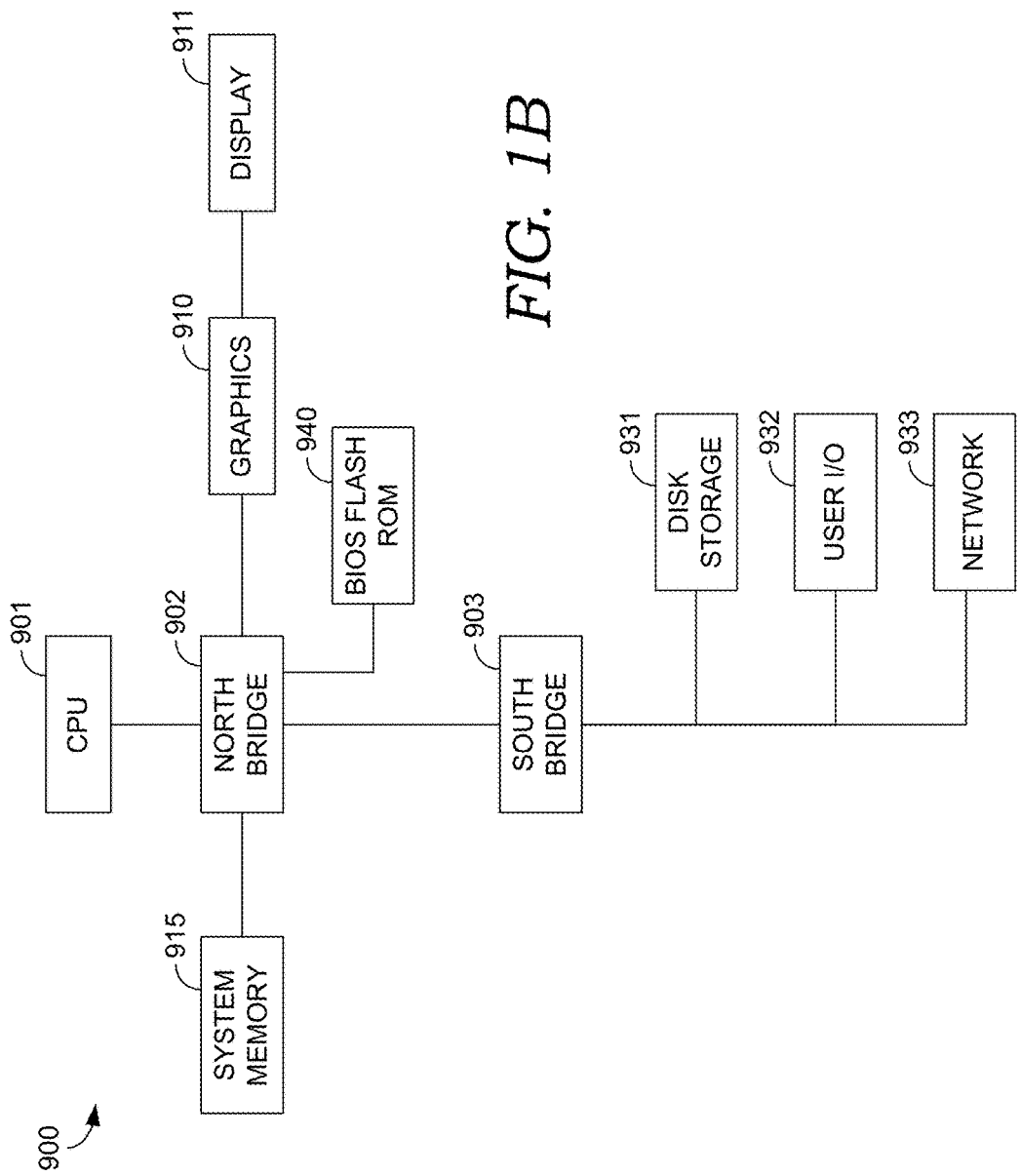

Turning briefly to FIG. 1B, there is shown one example embodiment of computing system 900 that has software instructions for storage of data and programs in computer-readable media. Computing system 900 is representative of a system architecture that is suitable for computer systems such as computing system 120. One or more CPUs such as 901, have internal memory for storage and couple to the north bridge device 902, allowing CPU 901 to store instructions and data elements in system memory 915, or memory associated with graphics card 910, which is coupled to display 911. Bios flash ROM 940 couples to north bridge device 902. South bridge device 903 connects to north bridge device 902 allowing CPU 901 to store instructions and data elements in disk storage 931 such as a fixed disk or USB disk, or to make use of network 933 for remote storage. User I/O device 932 such as a communication device, a mouse, a touch screen, a joystick, a touch stick, a trackball, or keyboard, couples to CPU 901 through south bridge 903 as well. The system architecture depicted in FIG. 1B is provided as one example of any number of suitable computer architectures, such as computing architectures that support local, distributed, or cloud-based software platforms, and are suitable for supporting computing system 120.

Returning to FIG. 1A, in an embodiment, computer system 120 is a computing system made up of one or more computing devices. In an embodiment, computer system 120 includes an adaptive multi-agent operating system, but it will be appreciated that computer system 120 may also take the form of an adaptive single agent system or a non-agent system. Computer system 120 may be a distributed computing system, a data processing system, a centralized computing system, a single computer such as a desktop or laptop computer or a networked computing system.

In an embodiment, computer system 120 is a multi-agent computer system with agents. A multi-agent system may be used to address the issues of distributed intelligence and interaction by providing the capability to design and implement complex applications using formal modeling to solve complex problems and divide and conquer these problem spaces. Whereas object-oriented systems comprise objects communicating with other objects using procedural messaging, agent-oriented systems use agents based on beliefs, capabilities and choices that communicate via declarative messaging and use abstractions to allow for future adaptations and flexibility. An agent has its own thread of control which promotes the concept of autonomy.

Figure 3:
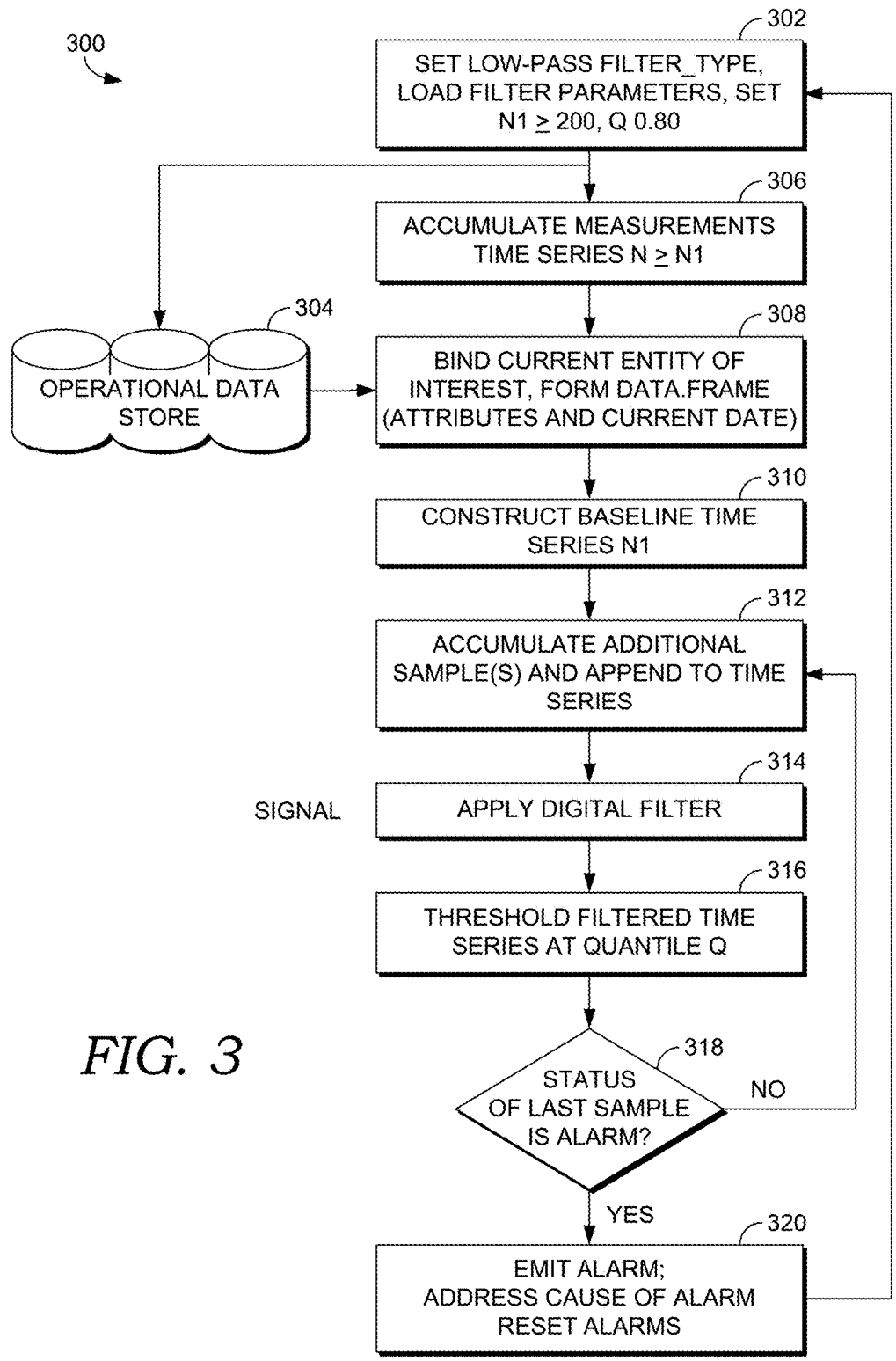
FIG. 3 depicts a flow diagram of a method for alarm filtering, in accordance with embodiments of the invention.
Figure 4A:
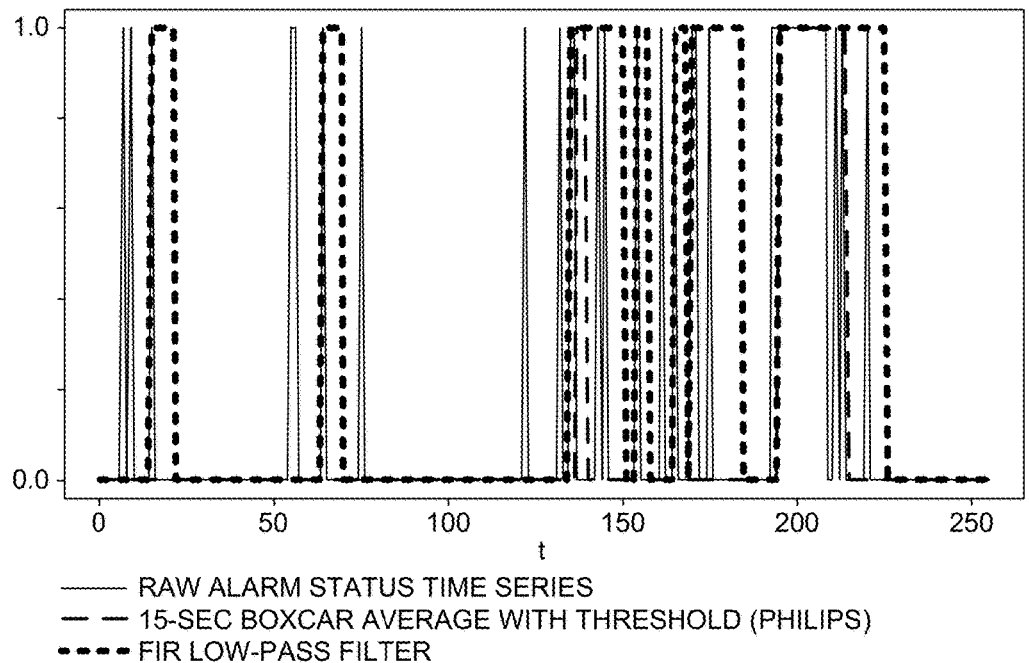
FIGS. 4A and 4B depict time series from one example case using FIR and 8th-Order Chebyshev embodiments, respectively.
Figure 4B:
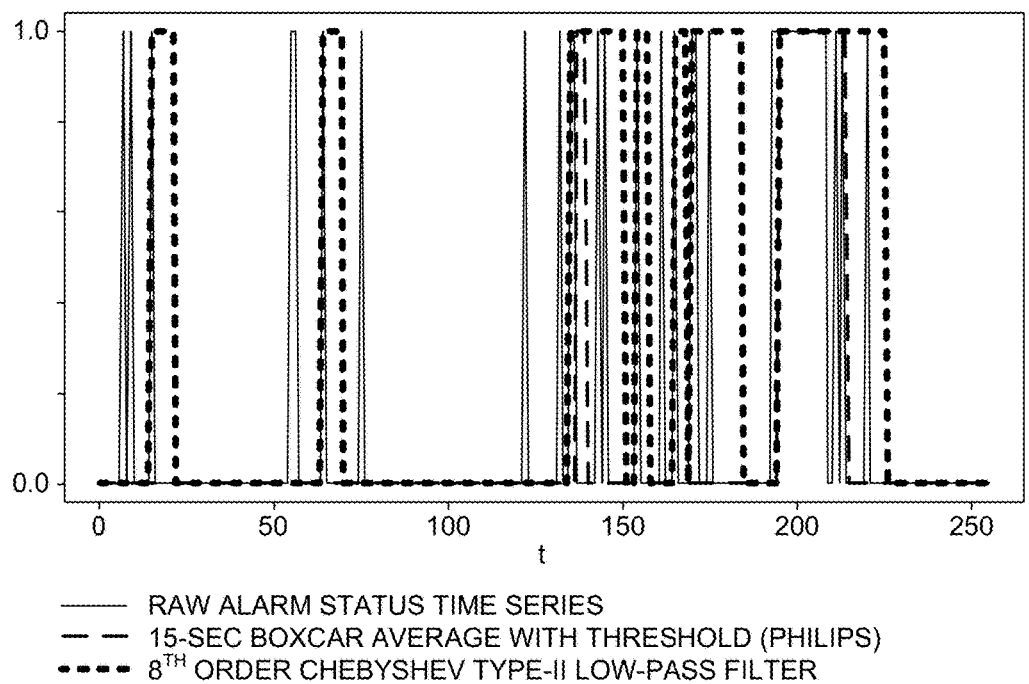
Figure 5:
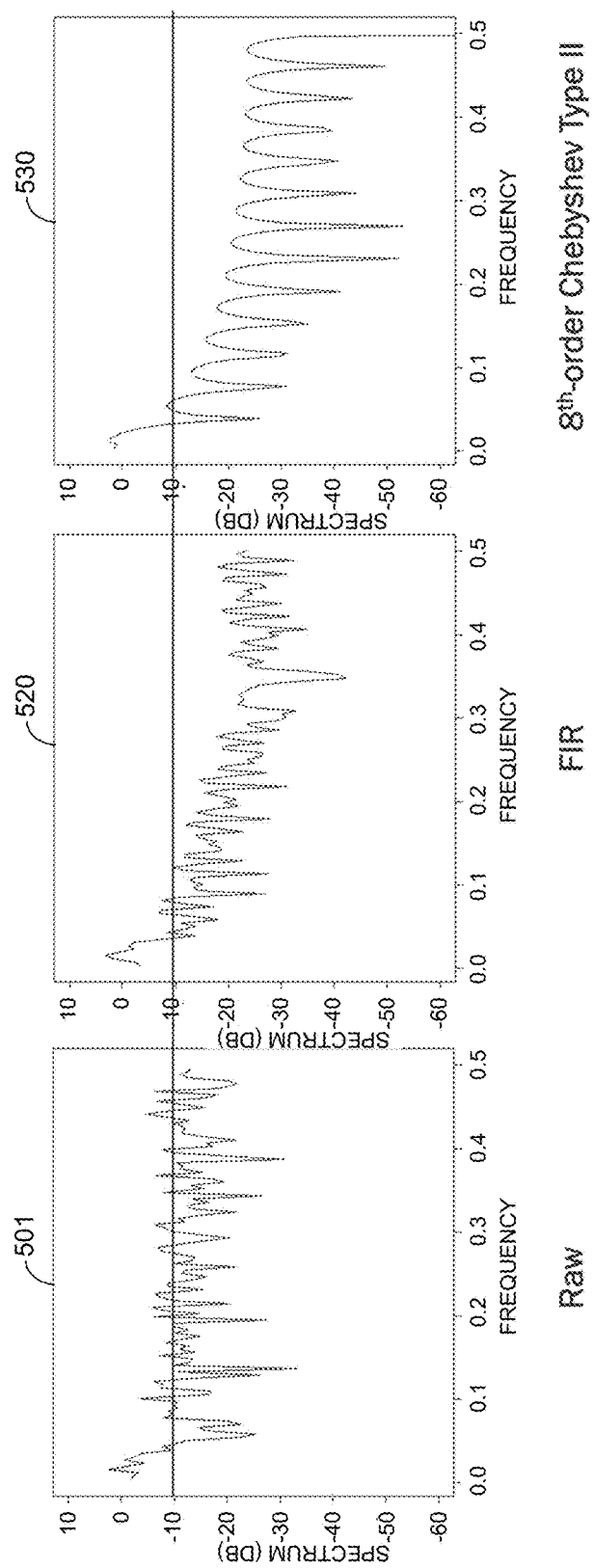
FIG. 5 depicts frequency amplitude spectra for an example case using FIR and 8th-Order Chebyshev embodiments.

Turning now to FIG. 3, there is depicted in 300 a representative flow diagram of clinical decision processing. At 302, operation begins when the equipment is turned on or when a clinician manually resets an alarm, to re-initialize operation. An alarm reset signal in general could be entered by a clinician at any time. In an embodiment, a clinician resets the alarm after being presented with data in 320, so that the operation returns to step 302. At 302, operation constraints for the method are set. In an embodiment a tuple of constraint parameters such as N1, Q and filter type are selected to constrain the operation of the algorithm. In an embodiment these constraint parameters are preset values determined separately for each physiological variable monitored. In an embodiment, a monitor options interface allows a clinician to tune the constraints for the particular application. In an embodiment these constraints are a function of an input operational context such as ICU, in-home, or clinical outpatient setting. In an embodiment, upon alarm reset and/or power up, preset values of N1, Q and filter type are used that are read from a configuration table.

In an embodiment, one or more constraint parameters are determined based on a number of factors dependent upon patient data such as measured heart rate, respiratory rate, blood pressure, oximetry data, or their processed values such as trends, averages, or rank order statistic results. In an embodiment, a number of factors are combined through a weighted combination of factors to determine a resultant constraint parameter for a patient. In an embodiment, if constraint parameters are determined for oximetry data, a patient's oximitry data is weighted heavily while the patient's heart rate and respiratory rate are weighted relatively less, and blood pressure is weighted even lower.

In an embodiment the filter type is a low pass filter. In an embodiment the low pass filter is a finite impulse response filter. In an embodiment the finite impulse response filter consists of a window of eight equal weight values to form an accumulator of eight adjacent samples. In an embodiment a low pass filter is an eighth order Chebyshev type 2 filter with 30 dB passband ripple, a critical frequency 0.075 times the nyquist frequency. In an embodiment the critical frequency is chosen to be 0.1 or 0.2 times the nyquist frequency. In an embodiment, a table of filters is indexed as a function of critical frequency, and a filter is chosen based on desired delay characteristics, or other indexing parameters or criteria. In an embodiment, the filter form is chosen from the set consisting of: chebyshev, butterworth, elliptical, finite impulse response, infinite impulse response, and savitzky-golay filters In an embodiment N1 is an input that prevents the method of computing quantile from running until there is a long enough time series to run a quantile estimation process. In an embodiment, measurements are accumulated until there are at least N1 samples. In an embodiment, a monitor emits alarms without a quantile filter on the physiological variable until there is sufficiently stable data of sufficient length to form a quantile estimate. In an embodiment, a clinician initiates quantile screening by visually monitoring the patient physiological variables for a stable pattern, and selecting a user interface control that indicates a baseline to initiate screened monitoring.

At 306 physiological variable data is persisted in a manner appropriate to the embodiment, buffering physiological variable data for local processing in monitor 141, sending data to a remote computer 120, or 140 and recording physiological variable data and/or binary alarm data in data store 121. Persisted data is stored in operational data store 304. At 308 a patient identity, and all other patient attributes are associated with the persisted physiological variable data. In an embodiment the physiological variable data is bound to a record of an entity (from a monitoring device or from an electronic medical record.) In an embodiment at 310 data is retrieved from operational store 304 to construct a baseline segment of length N1. In an embodiment, at 312 no additional samples are accumulated the first time through the flow chart, but N1 samples are appended to the time series on subsequent returns to 312. In an embodiment, at 312 an additional N2 samples are appended to the segment of the time series analyzed. In an embodiment N2 samples are discarded from the segment analyzed. In an embodiment at 314 a segment of size N1+N2 is analyzed. In an embodiment N1+N2=N*K. In an embodiment N1=N2=N, and K=2. In an embodiment N2=1.

At 314 the predetermined digital filter is applied to the baseline time series. In an embodiment the Signal library package of R system is used to perform filter operations on the underlying time series. At 136 the resultant time series is processed using quantile estimation. In an embodiment at 136 a preliminary alarm is set for those sample indeces that exceed the determined quantile level (e.g. 80%). In an embodiment, an alarm is set if the most recent filtered alarm data exceeds the determined quantile level.

At 318 a preliminary alarm indication generated at 136 is further screened based on a status signal of the raw binary alarm indication signal. In an embodiment the most recent binary alarm indication signal is compared with the reference preliminary alarm indication, and if both indicate an alarm, then an alarm indication is emitted at 320 and the process returns to 302 after the alarm has been reset; otherwise no alarm indication is emitted and the process returns to 312. In an embodiment, a delay of the raw time series is made which is approximately equal to the group delay of the filtered time series so that the status comparison at 318 effects a comparison in roughly time-aligned fashion. In an embodiment, the most recent raw signal is used as a basis of comparison even though there is some delay inherent in the filtered signal. In an embodiment, the delay of the underlying filter is intentionally increased to a selected amount of alarm data (e.g. 20 seconds), but to effectively provide an uncorrelated second trial of alarm observation in the event of an alarm (e.g. an intentional delay of near 20 seconds when using a FIR filter with 20 second delay length). A delay within about 25% of the line length may be effectively uncorrelated.

In an embodiment decision support comprises:
1. Acquire a time series of N1 samples of serial physiologic measurements for analysis.
2. Bind the record of an entity (from a monitoring device or from an electronic medical record).
3. Retrieve the associated time series data (current data set, plus one or more reference time series).
4. Apply a low-pass digital filter to the time series.
5. Apply a quantile threshold to dichotomize the filtered time series. (Determine a preliminary alarm condition if the time series is above the quantile threshold).
6. Determine whether the last sample in the time series has a status equal to 1 denoting 'alarm'.
7. If the status equals 1, then determine that a preliminary alarm condition should be emitted as an alarm. If the status equals 0, then suppress or censor an alarm condition if said alarm condition exists.

By way of example, an embodiment as described in connection to FIGS. 1 through 3 and 7 was reduced to practice using two alternative filter designs giving the results shown in FIGS. 4 through 5 and 6A and 6B. Reduction to practice was accomplished using a computer running the Linux operating system, the open-source statistical software package R and the R module signal. Stream processing of the accruing time series was accomplished using IBM InfoSphere Streams™ stream-processing software. In this regard, a cloud-based computing configuration is one alternative preferred embodiment. Alternatively, a stand-alone server or other computing device equipped with suitable connectivity to the device(s) by which the time series are acquired may likewise be utilized in another embodiment.

From data acquired from in-patient hospital subjects and stored in an organization data warehouse, baseline time series as short as 200 samples long were found effective in establishing a stable frequency spectrum of the filtered $SpO_2$ time series. The same was found for heart rate, systolic blood pressure, mean arterial pressure, temperature, and other biomarkers that have been studied. In 72 hours of continuous SpO2 monitoring, only 1 false detections were declared (FP rate=0.01/hr).

Based on the alarm indication generated, information related to the alarm is provided for eventual presentation to a clinician. In an embodiment, the identified region is associated by the method with a particular form of alarm signal to alert the appropriate clinician in the most effective way for the particular region of the alarm. For example, when the value of the SpO2 sensor has been determined to be dangerously low one or more of the patient identity, the location of the patient, the level of the SpO2 physiological variable, and the trend statistic of the SpO2 physiological variable, are recorded within memory to be provided to a clinician who is alerted to the alarm condition. The method then provides the data necessary to give one or more of a visual text, a visual cue, auditory tone, or a verbal annunciator informs the clinician, such that the clinician is informed that "patient Bob Smith in room 102 has dangerously low value of SpO2, current level is 91% and falling." In an embodiment a clinician monitors one or more patients in a population, and simultaneously carries out other work orders, or other necessary tasks, or is attending to other patients, or is on call, and is notified of a generated alarm indication.

An embodiment of an alarm indication is one or more of a record indicating that an alarm region is present, permitting a clinician interface such as interface 142 to present at 320 a particularly modulated warning tone (loudness and interruption rate start at a recognizable level and increase to indicate severity of risk), an annunciator, a visual display of a message, a pop-up window on a computer screen, a banner, contextual vital statistics, a determined patient state, a selected action plan, a sequence of visual displays such as video of a room changing color to red and to black, and/or flashing on a map of the facility, transmitting a notification of an alarm state, sending a text message indicating the alarm state, transmitting a message that triggers another computer or communication system to trigger an alarm state in a remote machine, transmitting a message describing an alarm condition and making a computer record of the existence of an alarm condition, and maintaining a record to indicate current alarm state.

In an embodiment, information provided by the method comprises information related to one or more of: determining the effect of one or more drugs, determining the effect of one or more medical interventions, supporting extubating the patient, suggesting extubating the patient, supporting adjustment of patient therapy, supporting an adjustment to medication, suggesting an adjustment to patient therapy, supporting ventilator settings, suggesting adjusting ventilator settings, weaning the patient off ventilation, suggesting weaning the patient off ventilation, assessing patient status before surgery, assessing patient status during surgery, assessing patient status after surgery, assessing patient status before a medical procedure, assessing patient status during a medical procedure, assessing patient status after a medical procedure, monitoring for air leaks, monitoring for improper ventilation, monitoring exercise, monitoring stress levels, monitoring a medical condition and monitoring disease.

In support of presenting information related to the region to a clinician, at an embodiment evaluates the patient state. In an embodiment, available data such as data from data store 121 that pertains to the patient and/or current physiological variable values of monitored physiological parameters, is collected and fed into an analysis and decision engine such as a decision tree classifier that hypothesizes one or more conditions that may be the underlying cause of available data and/or the current alarm region. In an embodiment, the list of potential causes is presented to the clinician, in an embodiment, presented with estimates of likelihood or severity, or in rank order of likelihood or severity. In an embodiment, the list of possible conditions is pruned based on likelihood, severity, or on sound medical reasoning or protocol to determine a single hypothesis to be presented to a clinician. In an embodiment, redundant probes measure the same physiological variable, and patient state is determined based on evaluating the statistics for each probe.

In an embodiment, multiple physiological variable decision statistics and/or quantile statistics from multiple probes are combined to determine patient state, which in turn, are used to select an action plan as indicated. For example, the method may determine based in part on an emitted alarm that monitor 145 credibly indicates that the patient is awake, and monitor 144 credibly indicates that the patient is in a restless or agitated state, and monitor 146 credibly indicates an unusually low respiration rate, and monitor 141 credibly indicates low SpO2; therefore, a diagnostic decision tree hypothesizes tracheal blockage, and the method generates a recommendation to the clinician that a Heimlich maneuver should be attempted first, and then artificial emergency respiration, and if the patient begins to turn blue, an emergency tracheotomy should be performed.

In an embodiment, a centralized system of alarm threshold distribution insures that some binary alarms are generated for each patient by monitor 141. The raw binary alarms are then monitored for a patient based on an intentional generation of binary alarms, which are then subsequently filtered by central management. A raw-alarm measurement time period such as every five minutes is set up. In an embodiment, the raw-alarm measurement period is selected to be the time over which 10 raw alarms are expected. The number alarms generated during the raw-alarm time period is counted. The number of screened alarms is also counted. The counts are persisted, and alarm rates are recorded and used as a metric to determine if the centralized alarm strategy is effective. If the counts are inconsistent with the desired strategy, the alarm threshold adjusted in an attempt to achieve the desired result. For example, if a patient is expected to generate 10 raw alarms every five minutes at a setting of 89, and only 2 raw alarms are experienced, then the threshold is adjusted upward by about 2% of the nominal amount, so that a threshold of 91 is sent to monitor 141, and monitor 141 confirms the use of the threshold of 91 by sending an acknowledge message to patient manager 140. In an embodiment, a test procedure is periodically run when the status of the patient is relatively stable. For example, a central monitor program running in EHR 160 predicts that the monitored physiological variable will be non-alarm over the next 30 seconds, and so adjusts the alarm threshold up to 100 (effectively forcing the binary alarm signal to 1 for all samples). After 10 seconds, the central monitoring program counts 10 alarms, and so re-adjusts the threshold back to 91, having thus confirmed that the sensor is working, and initializes the filter state to mask the forced alarms.

Although the invention has been described with reference to the embodiments illustrated in the attached drawing figures, it is noted that substitutions may be made and equivalents employed herein without departing from the scope of the invention as recited in the claims. For example, additional steps may be added and steps omitted without departing from the scope of the invention.

Many different arrangements of the various components depicted, as well as components not shown, are possible without departing from the spirit and scope of the present invention. Embodiments of the invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the invention.

It will be understood that certain features and subcombinations are of utility and may be employed without reference to other features and subcombinations and are contemplated within the scope of the claims. Not all steps listed in the various figures need be carried out in the specific order described.

The invention claimed is:

1. One or more non-transitory computer storage media storing computer-useable instructions that, when used by one or more computing devices, cause the one or more computing devices to perform operations comprising:
   receiving one or more monitored physiological variables of a patient;
   forming a time-series with binary alarm signals over a first time interval, wherein the binary alarm signals indicate either a presence or absence of an alarm condition based on the one or more physiological variables, and wherein the time-series comprises a chronologically ordered set of time windows including a first time window and a last time window;
   applying a low pass filter operation to the time-series of binary alarm signals to produce a resultant filtered signal;
   generating a preliminary alarm condition by performing a rank order filter operation on the resultant filtered signal;
   screening the preliminary alarm condition against a binary alarm signal included in the last time window of the time-series of binary alarm signals; and responsive to the preliminary alarm condition and the binary alarm signal included in the last time window indicating the presence of an alarm condition, presenting an indication of an alarm.

2. The computer-readable media of claim 1, wherein said rank order filter operation comprises a quantile operation based on a predetermined quantile fraction Q.

3. The computer-readable media of claim 2, wherein said quantile fraction Q is chosen within an interval that is greater than 50 percent.

4. The computer-readable media of claim 2, wherein said quantile fraction Q is chosen within an interval that is greater than 85 percent.

5. The computer-readable media of claim 2, wherein said low pass filter operation performs at least 10 dB of sidelobe suppression for frequencies at least 10 percent above the nyquist frequency.

6. The computer-readable media of claim 5, wherein said low pass filter is synthesized based on at least one of chebyshev, butterworth, elliptical, finite impulse response, infinite impulse response, and savitzky-golay filters.

7. A computer-implemented method to evaluate an alarm condition for a monitored patient within a population of one or more patients, the method comprising:
    determining a quantile threshold for a patient in a population, initializing a monitor and generating a time-series binary raw alarm signal, wherein the time-series comprises a chronologically ordered set of time windows including a first time window and a last time window;
    receiving an alarm indication based on applying a low pass filter operation to the binary alarm signal to produce a filtered binary alarm signal, generating a preliminary alarm condition by performing a rank order filter operation on the filtered binary alarm signal, and determining when a predetermined sampling time the preliminary alarm condition exceeds a quantile threshold and a raw binary alarm signal sample are both present; and
    responsive to the determination that the preliminary alarm condition and the binary alarm signal are both present, communicating an indication of an alarm.

8. The computer-implemented method according to claim 7, further comprising presenting pie chart of need allocations to a clinician.

9. The computer-implemented method according to claim 8, further comprising deriving the quantile threshold for a patient from the pie chart of need allocations as adjusted by the clinician.

10. One or more non-transitory computer storage media storing computer-useable instructions that, when used by one or more computing devices, cause the one or more computing devices to perform operations comprising:
    acquiring a plurality of physiological signals from a sensor of patient physiology, the physiological signal corresponding to one or more monitored variables of a patient;
    forming a time-series of binary alarm signals over a first time interval, wherein the binary alarm signals indicate either a presence or absence of an alarm condition based on the plurality of physiological signals, and wherein the time-series comprises a chronologically ordered set of time windows including a first time window and a last time window;
    applying a low pass filter operation to the time-series of binary alarm signals to produce a resultant filtered signal;
    generating a preliminary alarm condition by evaluating a quantile threshold of the resultant filtered signal;
    screening the preliminary alarm condition against a binary alarm signal included in the last time window of the time-series of binary alarm signals; and
    based on the screening presenting an indication of an alarm when both the preliminary alarm condition is present and the binary alarm signal included in the last time window last sample raw alarm condition is present.

11. The computer-readable media of claim 10, wherein the low pass digital filter has at least an eight sample delay.

12. The computer-readable media of claim 10, wherein the low pass digital filter is chosen from the set consisting of: a Finite Impulse Response (FIR) filter, a Chebyshev filter, a Butterworth filter, and a Savitzky-Golay filter.

13. The computer-readable media of claim 12, further comprising calculating a degree of deviation from a running central tendency by using a quantile breakpoint-detection statistic performed on the processed result.

14. The computer-readable media of claim 13, wherein filtering the preliminary alarm condition based on a raw alarm condition includes comparing the breakpoint-detection result with an alarm status of the monitor that produced the raw binary alarm-status signal.

15. The computer-readable media of claim 11, wherein evaluating a quantile threshold of the processed result comprises using a baseline sample length of at least 200 samples long.

16. The computer-readable media of claim 13, wherein a quantile threshold is at least 80%.

17. The computer-readable media of claim 13, wherein a quantile threshold is at least 90%.

* * * * *

UNITED STATES PATENT AND TRADEMARK OFFICE
CERTIFICATE OF CORRECTION

PATENT NO.        : 10,610,160 B1
APPLICATION NO.   : 14/689343
DATED             : April 7, 2020
INVENTOR(S)       : Douglas S. McNair Page 1 of 2

It is certified that error appears in the above-identified patent and that said Letters Patent is hereby corrected as shown below:

In the Specification

Column 06, Line 65: Please remove "oximitry" and replace with --oximetry--.
Column 07, Line 45: Please remove "Chebyschev" and replace with --Chebyshev--.
Column 10, Line 20: Please remove "hypotaxia" and replace with --hypoxia--.
Column 10, Line 40: Please remove "Capilary Web" and replace with --Capillary Wedge--.
Column 14, Line 41: Please remove "oximitry" and replace with --oximetry--.
Column 14, Line 59: After "filters" please insert --.--.
Column 15, Line 33: Please remove "indeces" and replace with --indices--.

In the Claims

Column 19, Line 05: Please remove "computer-readable media" and replace with --non-transitory computer storage media--.
Column 19, Line 08: Please remove "computer-readable media" and replace with --non-transitory computer storage media--.
Column 19, Line 11: Please remove "computer-readable media" and replace with --non-transitory computer storage media--.
Column 19, Line 14: Please remove "computer-readable media" and replace with --non-transitory computer storage media--.
Column 19, Line 18: Please remove "computer-readable media" and replace with --non-transitory computer storage media--.
Column 20, Line 27: Please remove "computer-readable media" and replace with --non-transitory computer storage media--.
Column 20, Line 27: Please remove "computer-readable media" and replace with --non-transitory computer storage media--.
Column 20, Line 29: Please remove "computer-readable media" and replace with --non-transitory computer storage media--.
Column 20, Line 25: After "window" please remove "last sample raw alarm condition".

Signed and Sealed this
Twenty-second Day of December, 2020

Andrei Iancu
*Director of the United States Patent and Trademark Office*

CERTIFICATE OF CORRECTION (continued)
U.S. Pat. No. 10,610,160 B1

Column 20, Line 33: Please remove "computer-readable media" and replace with --non-transitory computer storage media--.
Column 20, Line 37: Please remove "computer-readable media" and replace with --non-transitory computer storage media--.
Column 20, Line 42: Please remove "computer-readable media" and replace with --non-transitory computer storage media--.
Column 20, Line 46: Please remove "computer-readable media" and replace with --non-transitory computer storage media--.
Column 20, Line 48: Please remove "computer-readable media" and replace with --non-transitory computer storage media--.